United States Patent
Li et al.

(10) Patent No.: US 11,639,328 B2
(45) Date of Patent: May 2, 2023

(54) METHOD FOR PREPARING AMANTADINE

(71) Applicant: SHANDONG HOLLY PHARMACEUTICAL CO., LTD., Shandong (CN)

(72) Inventors: Lanhua Li, Shandong (CN); Yuenan Qiu, Shandong (CN); Donghong Xu, Shandong (CN); Zhiyuan Liu, Shandong (CN); Huaqiang Wu, Shandong (CN); Zhufeng Zhou, Shandong (CN); Lihong Chen, Shandong (CN); Zhen Lin, Shandong (CN)

(73) Assignee: Shandong Holly Pharmaceutical Co., Ltd., Shandong (CN)

( * ) Notice: Subject to any disclaimer, the term of this patent is extended or adjusted under 35 U.S.C. 154(b) by 203 days.

(21) Appl. No.: 17/287,793

(22) PCT Filed: May 19, 2020

(86) PCT No.: PCT/CN2020/091025
§ 371 (c)(1),
(2) Date: Apr. 22, 2021

(87) PCT Pub. No.: WO2021/232232
PCT Pub. Date: Nov. 25, 2021

(65) Prior Publication Data
US 2022/0251023 A1    Aug. 11, 2022

(51) Int. Cl.
*C07C 209/74* (2006.01)
*C07C 211/38* (2006.01)

(52) U.S. Cl.
CPC .......... *C07C 209/74* (2013.01); *C07C 211/38* (2013.01); *C07C 2603/74* (2017.05)

(58) Field of Classification Search
USPC ....................................................... 564/458
See application file for complete search history.

(56) References Cited

U.S. PATENT DOCUMENTS 4,122,193 A    10/1978  Scherm et al.

FOREIGN PATENT DOCUMENTS

| CN | 101041622 A | 9/2007 |
|---|---|---|
| CN | 107445848 A | 12/2017 |
| CN | 109535004 A | 3/2019 |

*Primary Examiner* — Ana Z Muresan
(74) *Attorney, Agent, or Firm* — Laurence A. Greenberg; Werner H. Stemer; Ralph E. Locher

(57) ABSTRACT

A method for preparing amantadine includes chlorinating adamantane with chlorine gas in a solvent in the presence of a Lewis acid catalyst to obtain a reaction liquid, and then removing the solvent and residues containing the catalyst in the reaction liquid, to obtain a chlorinated product. The chlorinated product is mixed with urea to a mixture, and the mixture is subjected to an amination reaction, to obtain amantadine. The results of examples show that the purity of the prepared amantadine could reach 99.5% or more.

19 Claims, No Drawings

METHOD FOR PREPARING AMANTADINE

BACKGROUND OF THE INVENTION

Field of the Invention

The present disclosure relates to the technical field of the preparation of medicine, and in particular to a method for preparing amantadine.

Description of the Related Art

Amantadine, also known as tricyclodecane, can be used for prevention and early treatment of Asian-11 influenza, and in combination with antibiotic for treatment of sepsis and viral pneumonia, and also has functions of reducing fever and anti-parkinsonian.

At present, amantadine is mainly prepared by brominating adamantane to obtain a brominated adamantane, and then reacting with urea. Brominating adamantane is performed by the reaction of adamantane with bromine, during which excess bromine needs to be added, and remaining bromine after reacting needs to be removed with sodium sulfite solution. The brominated amantane also needs to be washed and dried before subsequently reacting with urea. In addition, bromine used in this method is expensive, has strong corrosive, and is difficult to recover, which not only results in a high cost of adamantane, but also produces a lot of three wastes that pollute the environment.

SUMMARY OF THE INVENTION

In order to address the above defects in the prior art, the present disclosure provides a method for preparing amantadine. The preparation method provided by the present disclosure enables utilizing inexpensive chlorine gas to prepare amantadine, making the preparation cost low and the amount of three wastes produced small.

A method for preparing amantadine, comprising, (1) chlorinating adamantane with chlorine gas in a solvent in the presence of a Lewis acid catalyst to obtain a reaction liquid, and then removing the solvent and residues containing the catalyst in the reaction liquid, to obtain a chlorinated product; and (2) mixing the chlorinated product with urea to a mixture, and subjecting the mixture to an amination reaction, to obtain amantadine.

In some embodiments, the chlorinating adamantane with chlorine gas is performed at a temperature of $-10°$ C. to $10°$ C.

In some embodiments, the Lewis acid is at least one selected from the group consisting of ferric chloride, aluminum chloride and tungsten hexachloride.

In some embodiments, a weight ratio of adamantane to the Lewis acid is in the range of 1:(0.01-0.1).

In some embodiments, a weight ratio of adamantane to the chlorine gas is in the range of 1:(0.37-0.55).

In some embodiments, the solvent is haloalkane and/or halogenated aromatics.

In some embodiments, a weight ratio of adamantane to the solvent is in the range of 1:(1-10).

In some embodiments, the chlorinated product is a mixture of monochloroadamantane and adamantane, wherein a weight ratio of monochloroadamantane to adamantane in the chlorinated product is in the range of (65-90):(35-10).

In some embodiments, a weight ratio of the chlorinated product to urea is in the range of 1:(0.25-0.35).

In some embodiments, the amination reaction is specified as follows: after mixing the chlorinated product with the urea, the resulting mixture is heated to a temperature of $165°$ C. to $185°$ C. to start the amination reaction; the temperature is naturally raised to $200°$ C. to $250°$ C., and then the resulting reactant is maintained at this temperature for a period of time.

In some embodiments, the method further comprises after the amination reaction, subjecting the aminated product to a post-treatment, wherein the post-treatment comprises the following steps: dissolving the aminated product in an acid, filtering, and adjusting pH value of the resulting filtrate to 6-7, to precipitate out amantadine.

In some embodiments, the acid is hydrochloric acid or sulfuric acid.

In some embodiments, the residue after filtering is adamantane, and the adamantane is returned to the chlorination step.

The present disclosure provides a method for preparing amantadine, comprising: (1) chlorinating adamantane with chlorine gas in a solvent in the presence of a Lewis acid catalyst to obtain a reaction liquid, and then removing the solvent and residues containing the catalyst in the reaction liquid, to obtain a chlorinated product; and (2) mixing the chlorinated product with urea to a mixture, and subjecting the mixture to an amination reaction, to obtain amantadine. In the present disclosure, inexpensive chlorine gas is used to prepare amantadine, making the preparation cost low and the product purity high, and at the same time, avoiding the problem of difficulty in the treatment of three wastes produced by the bromination. In the present disclosure, after the chlorination, only the solvent and residues containing the catalyst are removed, and the next step could be carried out without purifying the chlorinated product. This process is simple in operation steps, and the amount of three wastes produced by the same is small. Further, in the present disclosure, the unreacted adamantane could be reused, thereby further lowering the amount of the three wastes, and making the method of the present disclosure easier to industrial. The results of examples show that the purity of amantadine prepared in the present disclosure could reach 99.5% or more.

DETAILED DESCRIPTION OF THE INVENTION

The present disclosure will be further described below with reference to embodiments.

The present disclosure provides a method for preparing amantadine, comprising, (1) chlorinating adamantane with chlorine gas in a solvent in the presence of a Lewis acid catalyst to obtain a reaction liquid, and then removing the solvent and residues containing the catalyst in the reaction liquid, to obtain a chlorinated product; and (2) mixing the chlorinated product with urea to a mixture, and subjecting the mixture to an amination reaction, to obtain amantadine.

In the present disclosure, adamantane is chlorinated with chlorine gas in a solvent in the presence of a Lewis acid catalyst. According to the present disclosure, in some embodiments, the Lewis acid is at least one selected from the group consisting of ferric chloride, aluminum chloride and tungsten hexachloride. In some embodiments, a weight ratio of adamantane to the Lewis acid is in the range of 1:(0.01-0.1), preferably 1:(0.03-0.08). In some embodiments, a weight ratio of adamantane to chlorine gas is in the range of 1:(0.37-0.55), preferably 1:(0.4-0.5). In some embodiments, the solvent is haloalkane and/or halogenated aromatics, preferably dichloromethane or trichloromethane. In some embodiments, a weight ratio of adamantane to the solvent is in the range of 1:(1-10), preferably 1:(2-8).

According to the present disclosure, in some embodiments, the chlorinating adamantane with chlorine gas is performed at a temperature of $-10°$ C. to $10°$ C., preferably $-5°$ C. to $5°$ C. In the present disclosure, there are no special requirements on the time for the chlorination. In specific embodiments of the present disclosure, chlorine gas is stopped when the mass percentage of dichloroadamantane is more than 0.5% by TLC (thin-layer chromatography) monitoring.

In some embodiments of the present disclosure, adamantane and the Lewis acid are firstly dissolved in a solvent, then chlorine gas is introduced into the resulting solution at a temperature, and the mixture is subjected to the chlorination. In the present disclosure, there are no special requirements on the flow rate of chlorine gas, and it is possible to use any flow rate known to those skilled in the art. According to the present disclosure, adamantane is chlorinated with chlorine gas in the presence of a Lewis acid catalyst, in which using inexpensive chlorine gas instead of bromine in the traditional method makes the cost lower and more environmentally friendly.

According to the present disclosure, after the chlorination, the solvent and residues containing the catalyst in the reaction liquid are removed, to obtain a chlorinated product. According to the present disclosure, in some embodiments, the method for removing the solvent and residues containing the catalyst is distillation. In the present disclosure, there are no special requirements on the conditions for distillation, as long as the solvent and the residues containing the catalyst could be removed under such conditions. According to the present disclosure, the chlorinated product is monochloroadamantane and unreacted adamantane. In some embodiments, a weight ratio of monochloroadamantane to adamantane in the chlorinated product is in the range of (65-90):(35-10), specifically preferably 65:35, 70:30, 75:25, 80:20, 85:5 or 90:10. According to the present disclosure, in some embodiments, after completing distillation of the solvent, simple distillation is continued to obtain a mixture of monochloroadamantane and adamantane until no distillate is steamed out from the top of the column, and resulting materials at the bottom of the column is residues containing the catalyst. In the present disclosure, there are no special requirements on the temperature for distilling the solvent and the mixture of monochloroadamantane and adamantane, and it is possible to select the temperature according to actual needs. According to the present disclosure, the mixture is directly used for the next step without purifying monochloroadamantane, making the steps simpler and easier to operate, and the solvent obtained by distillation can be reused; therefore, the amount of three wastes produced in the whole process is small.

According to the present disclosure, after obtaining a chlorinated product, the chlorinated product is mixed with urea, and then subjected to an amination reaction, to obtain amantadine. According to the present disclosure, in some embodiments, a weight ratio of the chlorinated product to urea is in the range of 1:(0.25-0.35), preferably 1:0.3. According to the present disclosure, in some embodiments, the chlorinated product is directly mixed with solid urea without adding any solvent.

According to the present disclosure, the amination reaction is specified as follows: in some embodiments, after mixing the chlorinated product with urea, the resulting mixture is heated to a temperature of $165°$ C. to $185°$ C. to start the reaction, and the temperature is naturally raised to $200°$ C. to $250°$ C., and then the resulting reactant is maintained at this temperature for a period of time; in other embodiments, after mixing the chlorinated product with urea, the resulting mixture is heated to a temperature of $170°$ C. to $180°$ C. to start the reaction, and the temperature is naturally raised to $210°$ C. to $240°$ C., and then the resulting reactant is maintained at this temperature for a period of time. According to the present disclosure, in some embodiments, the resulting reactant is maintained at this temperature for 1 hour, and the reaction is finished when the mass percentage of monochloroadamantane is less than 0.3% by TLC monitoring. According to the present disclosure, after raising the temperature to $165°$ C. to $185°$ C., monochloroadamantane in the chlorinated product reacts with urea, during which the heat will be released so as to raise the temperature to $200°$ C. to $250°$ C.

In some embodiments of the present disclosure, after the amination reaction, the aminated product is subjected to a post-treatment, wherein the post-treatment comprises the following steps: dissolving the aminated product in an acid, filtering and separating unreacted adamantane, and adjusting pH value of the resulting filtrate with a liquid base to 6-7 to precipitate out the amantadine; and returning the unreacted adamantane to the chlorination step to continue the preparation of amantadine. In some embodiments, the acid is hydrochloric acid or sulfuric acid; a mass fraction of the hydrochloric acid is 30%, and a mass fraction of the sulfuric acid is 30%. The method according to the present disclosure makes it possible to recover the unreacted adamantane and reuse it, thereby further reducing the preparation cost, and to facilitate the reduction of the amount of three wastes.

The solutions provided by the present disclosure will be described in detail below with reference to the examples, but these examples should not be regarded as limiting the protection scope of the present disclosure.

Example 1

(1) 0.1 g of ferric trichloride and 1 g of adamantane were dissolved in 5 g of dichloromethane, then 0.37 g of chlorine gas was introduced at $0°$ C., and the resulting mixture was subjected to a chlorination reaction. The chlorine gas was stopped when the content of dichloroadamantane by TLC monitoring was more than 0.5%. The resulting liquid product was simply distillated to remove the solvent, the catalyst and the tar residue therein, obtaining a chlorinated product.

(2) The chlorinated product and solid urea were mixed in a mass ratio of 1:0.3, and heated to a temperature of $165°$ C. to start the reaction; then the temperature was naturally raised to $215°$ C., and they were maintained at the temperature for 1 hour; the reaction was finished when the content of monochloradiane by TLC monitoring was less than 0.3%. After finishing the reaction, the temperature was naturally decreased to ambient temperature, and the product was dissolved in a hydrochloric acid with a concentration of 30% and filtered (the residue after filtering was unreacted adamantane, and returned to step (1)), and the pH value of the resulting filtrate was adjusted to 6.5 with a liquid base to precipitate out a solid amantadine. The solid amantadine was filtered again and dried, obtaining amantadine. By testing, the obtained amantadine had a HPLC (high performance liquid chromatography) purity of 99.8%.

Example 2

(1) 0.01 g of aluminum trichloride and 1 g of adamantane were dissolved in 10 g of trichloromethane, then 0.55 g of chlorine gas was introduced at −5° C., and the resulting mixture was subjected to a chlorination reaction. The chlorine gas was stopped when the content of dichloroadamantane by TLC monitoring was more than 0.5%. The resulting liquid product was simply distillated to remove the solvent, the catalyst and the tar residue therein, obtaining a chlorinated product.

(2) The chlorinated product and solid urea were mixed in a mass ratio of 1:0.25, and heated to a temperature of 185° C. to start the reaction; then the temperature was naturally raised to 245° C., and they were maintained at the temperature for 1 hour; the reaction was finished when the content of monochloradiane by TLC monitoring was less than 0.3%. After finishing the reaction, the temperature was naturally decreased to ambient temperature, and the product was dissolved in a hydrochloric acid with a concentration of 30% and filtered (the residue after filtering was unreacted adamantane, and returned to step (1)), and the pH value of the resulting filtrate was adjusted to 7.0 with a liquid base to precipitate out a solid amantadine. The solid amantadine was filtered again and dried, obtaining amantadine. By testing, the obtained amantadine had a HPLC (high performance liquid chromatography) purity of 99.7%.

Example 3

(1) 0.05 g of tungsten hexachloride and 1 g of adamantane were dissolved in 6 g of trichloromethane, then 0.45 g of chlorine gas was introduced at −10° C., and the resulting mixture was subjected to a chlorination reaction. The chlorine gas was stopped when the content of dichloroadamantane by TLC monitoring was more than 0.5%. The resulting liquid product was simply distillated to remove the solvent, the catalyst and the tar residue therein, obtaining a chlorinated product.

(2) The chlorinated product and solid urea were mixed in a mass ratio of 1:0.35, and heated to a temperature of 180° C. to start the reaction; then the temperature was naturally raised to 235° C., and they were maintained at the temperature for 1 hour; the reaction was finished when the content of monochloradiane by TLC monitoring was less than 0.3%. After finishing the reaction, the temperature was naturally decreased to ambient temperature, and the product was dissolved in a hydrochloric acid with a concentration of 30% and filtered (the residue after filtering was unreacted adamantane, and returned to step (1)), and the pH value of the resulting filtrate was adjusted to 6.0 with a liquid base to precipitate out a solid amantadine. The solid amantadine was filtered again and dried, obtaining amantadine. By testing, the obtained amantadine had a HPLC (high performance liquid chromatography) purity of 99.7%.

The above description of the examples are only used to help understand the method of the present disclosure and its core idea. It should be pointed out that to those of ordinary skill in the art, the present disclosure could be improved and modified without departing from the principle of the present disclosure, and these improvements and modifications should fall within the scope of the claims of the present disclosure. Various modifications to these examples will be obvious to those skilled in the art, and the general principles defined herein may be implemented in other examples without departing from the spirit or scope of the present disclosure. Therefore, the present disclosure will not be limited to such examples shown herein, but will conform to the widest scope consistent with the principles and novel features disclosed herein.

What is claimed is:

1. A method for preparing amantadine, the method comprising:

chlorinating adamantane with chlorine gas in a solvent in a presence of a Lewis acid catalyst to obtain a reaction liquid, and then removing the solvent and residues containing the catalyst in the reaction liquid, to obtain a chlorinated product;

carrying out the chlorinating of the adamantane with chlorine gas at a temperature of −10° C. to 10° C.; selecting the Lewis acid from at least one of the group consisting of ferric chloride, aluminum chloride and tungsten hexachloride; providing a mixture of monochloroadamantane and adamantane as the chlorinated product; providing a weight ratio of adamantane to the Lewis acid in a range of 1:0.01-0.1; providing a weight ratio of adamantane to the chlorine gas in a range of 1:0.37-0.55; and mixing the chlorinated product with urea to obtain a mixture, and subjecting the mixture to an amination reaction, to obtain amantadine; after the amination reaction, subjecting the aminated product to a post-treatment; carrying out the post-treatment by dissolving the aminated product in an acid, filtering, and adjusting a pH value of a resulting filtrate to 6-7, to precipitate out amantadine; providing adamantane as the residue after filtering, and returning the adamantane to the chlorinating step.

2. The method according to claim 1, which further comprises providing at least one of haloalkane or halogenated aromatics as the solvent.

3. The method according to claim 1, which further comprises providing a weight ratio of adamantane to the solvent in a range of 1:1-10.

4. The method according to claim 1, which further comprises:

providing a weight ratio of the monochloroadamantane to the adamantane in the chlorinated product in a range of 65-90:35-10.

5. The method according to claim 1, which further comprises providing a weight ratio of the chlorinated product to the urea in a range of 1:0.25-0.35.

6. The method according to claim 1, which further comprises carrying out the amination reaction as follows:

after mixing the chlorinated product with the urea to obtain the mixture, heating the mixture to a temperature of 165° C. to 185° C. to start the amination reaction; and raising the temperature to 200° C. to 250° C., and then maintaining a resulting reactant at the temperature of 200° C. to 250° C. for a period of time.

7. The method according to claim 1, which further comprises selecting hydrochloric acid or sulfuric acid as the acid.

8. A method for preparing amantadine, the method comprising:

chlorinating adamantane with chlorine gas in a solvent in a presence of a Lewis acid catalyst to obtain a reaction liquid, and then removing the solvent and residues containing the catalyst in the reaction liquid, to obtain a chlorinated product; and mixing the chlorinated product with urea to obtain a mixture, and subjecting the mixture to an amination reaction, to obtain amantadine;

after the amination reaction, subjecting the aminated product to a posttreatment; and carrying out the post-treatment by dissolving the aminated product in an acid, filtering, and adjusting a pH value of a resulting filtrate to 6-7, to precipitate out amantadine.

9. The method according to claim 8, which further comprises carrying out the chlorinating of the adamantane with chlorine gas at a temperature of −10° C. to 10° C.

10. The method according to claim 8, which further comprises selecting the Lewis acid from at least one of the group consisting of ferric chloride, aluminum chloride and tungsten hexachloride.

11. The method according to claim 8, which further comprises providing a weight ratio of adamantane to the Lewis acid in a range of 1:0.01-0.1.

12. The method according to claim 8, which further comprises providing a weight ratio of adamantane to the chlorine gas in a range of 1:0.37-0.55.

13. The method according to claim 8, which further comprises providing at least one of haloalkane or halogenated aromatics as the solvent.

14. The method according to claim 8, which further comprises providing a weight ratio of adamantane to the solvent in a range of 1:1-10.

15. The method according to claim 8, which further comprises:
    providing a mixture of monochloroadamantane and adamantane as the chlorinated product; and
    providing a weight ratio of the monochloroadamantane to the adamantane in the chlorinated product in a range of 65-90:35-10.

16. The method according to claim 8, which further comprises providing a weight ratio of the chlorinated product to the urea in a range of 1:0.25-0.35.

17. The method according to claim 8, which further comprises carrying out the amination reaction as follows:
    after mixing the chlorinated product with the urea to obtain the mixture, heating the mixture to a temperature of 165° C. to 185° C. to start the amination reaction; and
    raising the temperature to 200° C. to 250° C., and then maintaining a resulting reactant at the temperature of 200° C. to 250° C. for a period of time.

18. The method according to claim 8, which further comprises selecting hydrochloric acid or sulfuric acid as the acid.

19. The method according to claim 8, which further comprises providing adamantane as the residue after filtering, and returning the adamantane to the chlorinating step.

* * * * *